(12) United States Patent
Utsugi

(10) Patent No.: US 6,936,064 B1
(45) Date of Patent: Aug. 30, 2005

(54) PIGMENTATION MAKEUP METHOD AND MAKEUP AUXILIARY USING IT, FLOOD LIGHT AND PACK

(75) Inventor: Ryuichi Utsugi, Tokyo (JP)

(73) Assignee: DRDC Limited, Tokyo (JP)

( * ) Notice: Subject to any disclaimer, the term of this patent is extended or adjusted under 35 U.S.C. 154(b) by 0 days.

(21) Appl. No.: 09/719,895

(22) PCT Filed: Jun. 22, 1999

(86) PCT No.: PCT/JP99/03323

§ 371 (c)(1),
(2), (4) Date: Dec. 19, 2000

(87) PCT Pub. No.: WO99/66882

PCT Pub. Date: Dec. 29, 1999

(30) Foreign Application Priority Data

Jun. 22, 1998 (JP) ........................................... 10-174859

(51) Int. Cl.[7] .............................................. A61N 33/00
(52) U.S. Cl. ........................................ 607/89; 607/88
(58) Field of Search .................................... 607/88–90

(56) References Cited

U.S. PATENT DOCUMENTS

| | | | | |
|---|---|---|---|---|
| 2,432,767 A | * | 12/1947 | Klein ............................ 2/174 |
| 5,307,523 A | * | 5/1994 | Lewis et al. .................... 2/433 |
| 5,557,112 A | * | 9/1996 | Csoknyai et al. ........ 250/504 R |
| 5,669,395 A | * | 9/1997 | Thompson ................... 128/846 |
| D423,712 S | * | 4/2000 | Aoki et al. ..................... D28/4 |
| D426,019 S | * | 5/2000 | Aoki et al. ..................... D28/4 |
| 6,502,583 B1 | * | 1/2003 | Utsugi ......................... 132/200 |

\* cited by examiner

*Primary Examiner*—Henry Bennett
*Assistant Examiner*—Nihir Patel
(74) *Attorney, Agent, or Firm*—Michael D. Bednarek; Shaw Pittman LLP

(57) ABSTRACT

The alleviation of the burden on the cosmetic decoration and the effect of making the subject to look thin can be easily accomplished by providing a technique of cosmetic decoration which easily obtains the same effect based on light and shade as the application of foundation, allows the beautiful state resulting from the cosmetic decoration to last for a fixed number of days without being impaired by water or perspiration, and produces a natural finish.

The method for cosmetic decoration according to this invention, in performing cosmetic decoration by resorting to the impartation of light and shade to the surface color of the skin, implements the cosmic decoration by causing the degree of pigment deposition in the area of the skin requiring to assume a darker color to be larger than in the other part of the skin thereby imparting light and shade to the surface color of the skin.

5 Claims, 6 Drawing Sheets

PIGMENTATION MAKEUP METHOD AND MAKEUP AUXILIARY USING IT, FLOOD LIGHT AND PACK

TECHNICAL FIELD

This invention relates to a technique for cosmetic decoration, particularly to a technique for cosmetic decoration intended to impart light and shade to the surface color of the skin.

BACKGROUND OF THE INVENTION

As the items that heavily weigh among the matters of concern for women, cosmetic decoration and slimness may be cited.

The cosmetic decoration largely varies the impression of a person who has used it. Of course, the object of this cosmetic decoration resides in satisfying the wish to be more beautiful. There are also times when the advantage of the change of the impression by cosmetic decoration manifested in altering the mode of feeling Is longed for and even materialized. From this point of view, the daily cosmetic decoration may well be called an act which women can perform with enjoyment.

Meanwhile, however, the cosmetic decoration can form a large burden for women. In the present situation in which the cosmetic decoration is recognized as what must be performed naturally, the sensation of burden inflicted on women possibly grows excessively because the act of performing the cosmetic decoration everyday may well be said in a sense as an obligation laid on woman.

The elements of the cosmetic decoration under discussion include eyebrow pencil, eye shadow, eye line, lip stick, foundation, etc. The cycbrow pencil, eye shadow, eye line, and lip stick are such in nature that they may be properly varied to suit the particular feeling created by a given woman on the particular day In contrast, the foundation does not need to be varied very much day by day because it is intended to emphasize the contour of a face by imparting light and shade roughly to the face throughout the entire area thereof. Actually, however, women are spending much time in applying the foundation evenly to their faces and they repeat this application any number of times daily because the foundation is caused to peel off with the elapse of time on exposure to water or perspiration. By forming the foundation which inherently necessitates no such repetition of application in a constitution fixed to a degree enough to obviate the necessity for the daily repetition of application under discussion, it is made possible to curtail the labor otherwise excessively spent concerning the cosmetic decoration.

Further, the foundation entails the complexity that it must be selected to match the color of the skin of an individual person intending to purchase it in addition to the complexity which pertains to the necessity for evenly applying it to the face. A great variety of foundations are marketed for the sake of ensuring natural finish of cosmetic decoration. Undeniably the probability that such a consumer will find a foundation perfectly fit for the color of her skin is low.

Another matter of concern for women is the slimming, i.e. reduction of the body weight. It is an evident fact that women fondly cherish the hope of becoming slim. Their wish at least to look slim exists certainly. In attempting to materialize this wish to look slim, they are allowed to utilize the technique of foundation mentioned above. That is, by applying a proper terminator of light and shade to arms and logs and emphasizing the parts of light and shade thereon, it is made possible to make a body look beautiful in harmonious modulation. The method called "body makeup" which recent actresses and models are exercising as during the course of filming constitutes itself the technique of foundation just mentioned. This method implies daily application of a foundation to arms and legs. Since the fulfillment of this method entails considerable trouble, it is nearly impossible for women at large to stick to the method faithfully.

The present invention has been perfected based on the concept illustrated above. It is aimed at providing a technique for cosmetic decoration which easily obtains the effect based on the same terminator of light and shade as is attained by the application of a foundation, enables the resultant beautiful state to last for a fixed number of days without entailing any collapse due to exposure to water or perspiration, and promises natural finish of the cosmetic decoration, thereby alleviating the burden of cosmetic decoration and easily bringing the effect of enabling a user to look thin.

Disclosure of the Invention

The present inventor has taken notice of the fact that as an agency for imparting light and shade to the skin and, at the same time, enabling the effect to last for a fixed number of days, the familiar natural phenomenon which is known as "suntan" originating in the deposition of melamine pigment exists and has eventually conceived of an idea that the problems mentioned above are solved by utilizing this natural phenomenon. The present inventor has pursued a further study based on this idea and has consequently perfected a method which, in performing cosmetic decoration targeted at imparting light and shade to the surface color of the skin, attains the cosmetic decoration by enlarging the degree of pigment deposition on the skin in the area requiring to assume a darker color and imparting light and shade to the surface color of the skin. Since the method for cosmetic decoration according to this invention which will be described herein below utilizes the deposition of pigment on the skin, it is at a great advantage in not only enabling the light and shade imparted to the skin to last for several weeks as a unit without being disturbed by perspiration or water but also finding general acceptance among woman because the method takes advantage of the popular phenomenon found in daily life. According to the present inventor's study, this method of cosmetic decoration has a further advantage. Specifically, when the skin is endowed with light and shade by this method of cosmetic decoration, the light and shade spontaneously becomes very natural in conformity with the tinge inherent in the skin of an individual person and ultimately gives rise to far more natural finish than is obtained by using any other foundation.

Several methods are available for the purpose of varying the degree of deposition of pigment in different areas of the skin. For example, the degree of pigment deposition in different areas of the skin can be varied by irradiating the skin with proper light. To be more specific, when the skin is irradiated with light other than the laser beam, the deposition of pigment can be caused to varying degrees in different areas of the skin by irradiating the areas of the skin requiring to acquire a darker color with the light in a proportionately larger dosage thereby causing the deposition of pigment to occur in varied degrees in the different areas of the skin. In other words, this method consists in imparting light and shade to the surface color of the skin by causing the skin to be burnt by the sunlight to varying degrees in different parts thereof thereby inducing the suntan (browning) proportionately to the varying degrees of the sunburn.

The suntan of the nature described above is produced irrespectively of distinction between visible light and invisible light, despite difference in degree. The term "light" as used in this invention embraces both visible light and invisible light. The suntan as generally known can be produced by using the ultraviolet light, for example. The suntan can occur when the skin is irradiated with light of any wavelength such as, for example, visible light, ultraviolet light, and far infrared rays. In terms of the ease with which the suntan is produced, however, it is considered most practical to use the ultraviolet light.

For the purpose of varying the degree of pigment deposition in different areas of the skin by the exposure to light other than the laser beam, it suffices to vary proportionately the dosage of the light on the skin in the different areas. That is, by irradiating the parts of the skin expected to acquire a darker color with the light of a larger dosage, it is made possible to vary properly the degree of pigment deposition in different areas of the skin. Though the kind of means to be adopted for varying the dosage of the light is irrelevant in this case, the variation may be attained by varying the wavelength of light, the dose of light per unit area, the time of irradiation, etc. In this case, one of such elements may be varied or two or more elements may be varied. Among other elements available for the variation, the variation of the dose of the light per unit area and the variation of the time of light irradiation in different areas of the skin prove particularly advantageous in terms of ease of execution. These two means find utility in a wide range because they can be implemented by using the sunlight and can effectively utilize both natural light and artificial light.

The variation of the dose of light per unit area can be effected, for example, by such a simple means as covering parts of the face with adhesive tape or by using a decorative aid furnished with a cover for hiding prescribed areas of the skin as described herein below. In this case, when the cover in the decorative aid is so formed as to allow easier passage of light in portions corresponding to the areas of the skin expected to acquire a darker color, the amounts of light allowed to irradiate different areas of the skin can be adjusted as expected by simply projecting light on the skin through the cover placed on the skin. Specifically, by gradationally varying the transparency of the cover to light in different portions of the cover or by deleting portions of the cover in the manner of openings, it is made possible to obtain a cover which is capable of manifesting the effect mentioned above. To be more specific, an adhesive tape which is provided with openings formed like slits can be effectively used in forming slender highlight zones in specific portions of the skin. The variation of the dosage of light by the variation of the time of light irradiation can be also accomplished by the decorative aid furnished with the cover. The cover in this case is preferred to consist of a plurality cover bodies adapted to hide prescribed ranges of the skin. Then, by sequentially removing these cover bodies while keeping the skin irradiated with light meantime, it is made possible to vary the time of light irradiation in different areas of the skin. Otherwise, the variation of the dose of light per unit area can be effected in the same manner as described above by using a projector which is provided with a light source adapted to emit a light capable of causing pigment deposition on the skin and a filter adapted to transmit the light from the light source. The filter in this case, when adapted to vary the transmittance thereof to light in different portions thereof or given the partial deletion described above, enables the light emitted to the skin positioned at a prescribed distance from the light source to irradiate the areas of the skin expected to acquire a darker color more than the other areas.

Though the description, as given above, concerns the case of using light other than the laser beam, this invention also contemplates varying the degree of pigment deposition in different areas of the skin by irradiating the skin with the laser beam. The theory for the application of the laser beam to the method for cosmetic decoration of the present invention is not so simple as in the case of using light other than the laser beam as described above. In the case of irradiating the skin with the laser beam, not only the dosage of the laser beam allowed to irradiate the skin but also the time for irradiating the skin with the laser beam have a large effect on the degree of pigment deposition on the skin. When the time of irradiation of the laser beam per round is shorter than the thermal relaxation time of the target pigment (the time required for one half of the absorbed thermal energy to complete migration into the ambient texture), the irradiation is enabled to induce omission of pigment instead of deposition of pigment. The Q switch oscillation ruby laser is disposed to produce pigment omission in the case of a high output and pigment deposition in the case of a low output. In the case of projecting the laser beam to the skin for the purpose of varying the degree of pigment deposition in different areas of the skin, therefore, the irradiation is enabled not only to promote the pigment deposition on the skin but also to induce omission of pigment in certain areas of the skin. Since the use of the laser beam makes it possible to produce omission of pigment which impedes pigment deposition in certain areas of the skin, it may be enabled to vary the degree of pigment deposition in different areas of the skin. Further, the method which uses the laser beam at all makes it possible to impart a brighter color to certain areas of the skin and, at the same time, a darker color to other areas of the skin and, therefore, brings the advantage of greatly widening the contrast between light and shade in different areas of the skin as compared with the case of utilizing the deposition of pigment exclusively. This is not the only advantage that is derived from using the laser beam. The fact that the variation of pigment deposition is allowed to occur in a large degree because of the use of the laser beam even when the time of irradiation of the skin is short may be cited as another advantage. Thus, the use of the laser beam results in successfully decreasing the burden imposed on a person who exercises cosmetic decoration in accordance with the method of this invention. Incidentally, since the laser beam used in imparting light and shade to the skin enables the boundary between light and shade to appear more distinctly, the impartation of light and shade can be applied to such narrow areas as are involved in the application of eye line or eye shadow.

For the laser beam under discussion, carbon dioxide gas laser, yag laser, alexandrite laser, etc. can be used besides the ruby laser mentioned above. The laser bean does not need to be particularly discriminated on account of the kind. The irradiation of the skin with the laser beam is generally carried out by causing the laser beam to scan a prescribed area of the skin. The degree of pigment deposition in different portions of the skin can be varied, for example, by varying the density, frequency, etc. of the scanning actions performed in different areas of the skin or by varying the wavelength of the laser beam. As regards the emission of the laser beam, the act of varying the degree of pigment deposition in different portions of the skin by using the decorative aid provided with the cover mentioned above may well be rated as a preferred embodiment of the laser irradiation.

Besides the use of the light in the manner described above, the impartation of light and shade to the surface color of the skin can be effected by using a pigment deposition promoting agent for promoting the deposition of pigment on the skin or the use of a whitening agent inhibiting pigment deposition on the skin. That is, by applying the pigment deposition promoting agent to the areas of the skin expected to acquire a darker color or by applying the whitening agent to the areas of the skin expected to acquire a brighter color, it is made possible to vary the degree of pigment deposition between these areas and other areas and impart variation to the light and shade of the surface color of the skin. Naturally, the whitening agent and the pigment deposition promoting agent mentioned above can be used in combination. As the pigment deposition promoting agent proper in this case, such chemical agents as psoralen which augment propagation of pigment cells and formation and secretion of melamine pigment and such chemical agents as dihydroxy acetone which induce deposition of pigment in cuticles by a different mechanism are usable. The melamine itself can be used as a pigment deposition promoting agent. Particularly when it is used in combination with such a chemical agent as liposome which promotes the seepage of melamine into the skin, the effect of interest is exalted. As concrete examples of the substance that is usable as the whitening agent, chemical agents possessed of the thyrosinase inhibiting activity effective in lowering the propagation and activation of pigment cells and inhibiting the synthesis of melanine pigment and chemical agents possessed of the endoserine inhibiting activity are conceivable. More specifically, γ-oryzanol, urocanic acid, titanium dioxide, oxybenzone, oxybenzone, salicylic acid, glycolic acid, α-hydroxy acid, linoleic acid, pionine, cysteine, glutathione, phenols, nitrofuran derivatives, ascorbic acid and derivatives thereof, compounds possessed of a SH group (glutathione, cystine, etc.), hydroquinone and dervatives thereof (hydroquinone monobenzyl ether, albutin, etc.), amines, kojic acid and derivatives thereof, oil-soluble licorice extract, mercuric chloride and derivatives thereof, PMH, vitamin A acid and derivatives thereof, azelaic acid, macranine, saran, methionine, lecithin, tranexainic acid, RIKIRICHIN, and endoserine inhibitor may be cited.

For the application of the pigment deposition promoting agent or the whitening agent to the skin, it suffices to apply it directly to the skin. Alternatively, a pack which is formed of a sheet adapted to be used as applied to the skin and has the parts of the sheet corresponding to the areas of the skin requiring to acquire a darker color coated or impregnated with a pigment deposition promoting agent capable of promoting deposition of a pigment or the parts of the sheet corresponding to the areas of the skin requiring to acquire a brighter color coated or impregnated with a whitening agent capable of inhibiting deposition of a pigment may be used. The pack of this construction is advantageous because it enables a pigment deposition promoting agent or a whitening agent to be easily and accurately applied to the necessary areas of the skin. In the sense that deposition of a pigment or omission of a pigment is effected with high accuracy in each of the specified areas of the skin, the method of interest can be applied instead of facial makeup to the impartation of light and shade to narrow areas of the skin. A tape which has a pigment deposition promoting agent or a whitening agent applied as incorporated in a tackifier to the side thereof intended to contact the skin may well be rated as advantageous in the sense that it can be stably fixed to the skin. The tape having the whitening agent applied thereto in the form of slender stripes in the direction of length, for example, affords a great convenience for the formation of highlight zones on the face. A sole pack which is formed by combining a pack coated or impregnated with the pigment deposition promoting agent and a pack coated or impregnated with a whitening agent is effective in further exalting the contrast of light and shade concerning the surface color of the skin.

BEST MODE OF EMBODYING THE INVENTION

Figure 1:
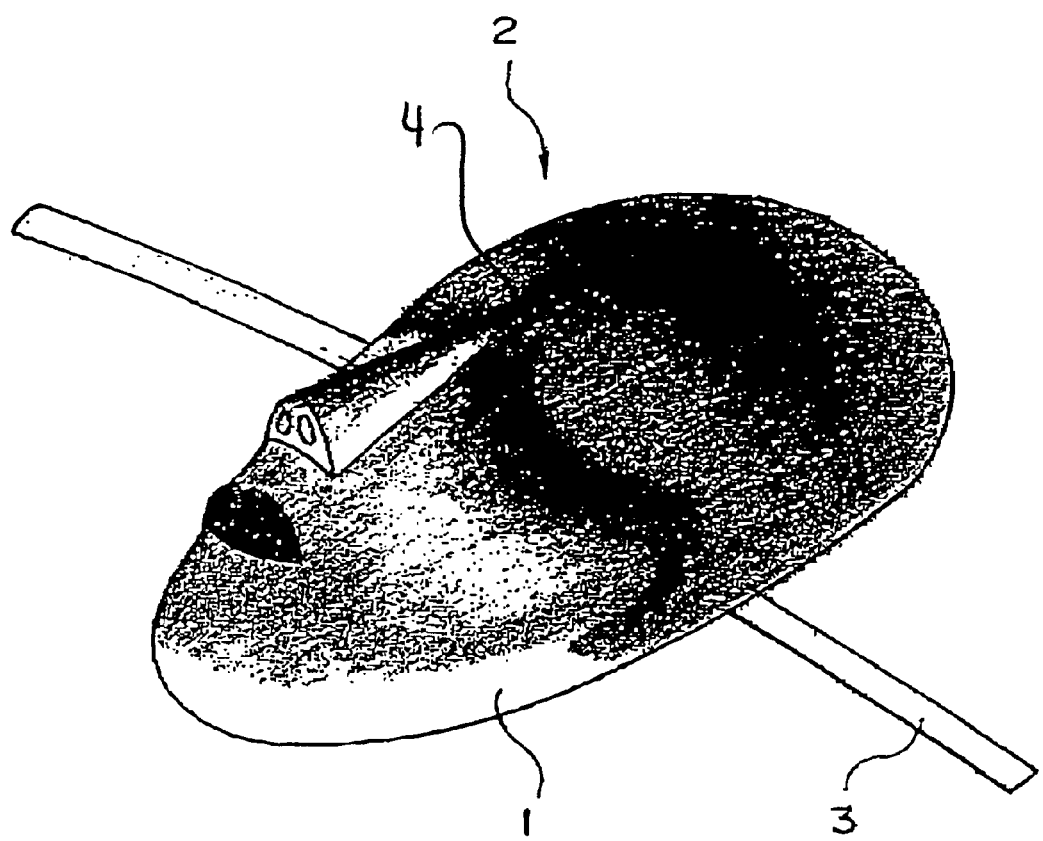
FIG. 1 is a perspective view illustrating a decorative aid to be used for the method of cosmetic decoration as the first mode of embodiment of this invention.

Now, preferred embodiments of this invention will be described below with reference to the drawings annexed hereto. In the description of the preferred embodiments, like parts will be denoted by like reference numerals to avoid repetition of description.

First Mode of Embodiment

As the first mode of embodiment, the method for cosmetic decoration will be described which comprises outlining a T zone against the surface of the face thereby obtaining the same effect as in performing the facial decoration resorting to proper variation of the application of a foundation.

This method of suntan makes a rule of effecting cosmetic decoration by using a decorative aid 2 which is provided with a mask 1 as a cover. This mask 1 has the T zone 4 of a face which is an area expected to assume a brighter color than in any other area and the portion which corresponds to the malar bone formed of a raw material impervious to the ultraviolet light and the other portions formed of a raw material pervious to the ultraviolet light. It further has the portions corresponding to the opposite lateral sides of a face which are the areas of the skin expected to assume the darkest color among other portions pervious to the ultraviolet light formed of a raw material transparent to the ultraviolet light. In short, this mask 1 has the portions thereof corresponding to the areas of a face requiring to emphasize the height formed of a raw material having proportionately low transparency to the ultraviolet light. The boundary between the portion pervious to the ultraviolet light and the portion impervious to the ultraviolet light is gradated to prevent the contrast between light and shade from becoming unnatural. The mask 1 is further provided with a fixing means 3 (refer to FIG. 1). to the ultraviolet light. The boundary between the portion pervious to the ultraviolet light and the portion impervious to the ultraviolet light is gradated to prevent the contrast between light and shade from becoming unnatural. The mask 1 is further provided with a fixing means 3 (refer to FIG. 1).

Now, the method of cosmetic decoration which uses this decorative aid 2. The wish to get a suntan by using this mask 1 is accomplished by first covering the face with the mask 1 and then fixing the mask 1 to the head with the fixing means 3. The face in the state consequently assumed is exposed for a prescribed time to the light of an ultraviolet lamp or the light such as sunlight which contains an ultraviolet light.

When this exposure to the light is made, the dosage of the ultraviolet light is eventually differentiated between the area of the skin corresponding to the portion of the mask 1 having high transparency to the ultraviolet light and the other area because this area receives the ultraviolet light in a larger amount per unit area. As a result, the opposite lateral sides of the face which have received a larger dosage of the ultraviolet light manifest the effect of the suntan strongly and the T zone which has received a smaller dosage of the ultraviolet light remains in a white state as the highlight zone and the intermediate part between these two different areas assume a state gradated from a light color to a dark color. Though the present mode of embodiment, as described above, uses the cover 1 which hides the entire area of the face, for example, this invention allows the cover 1 to hide only part of the face.

Second Mode of Embodiment

Figure 2:
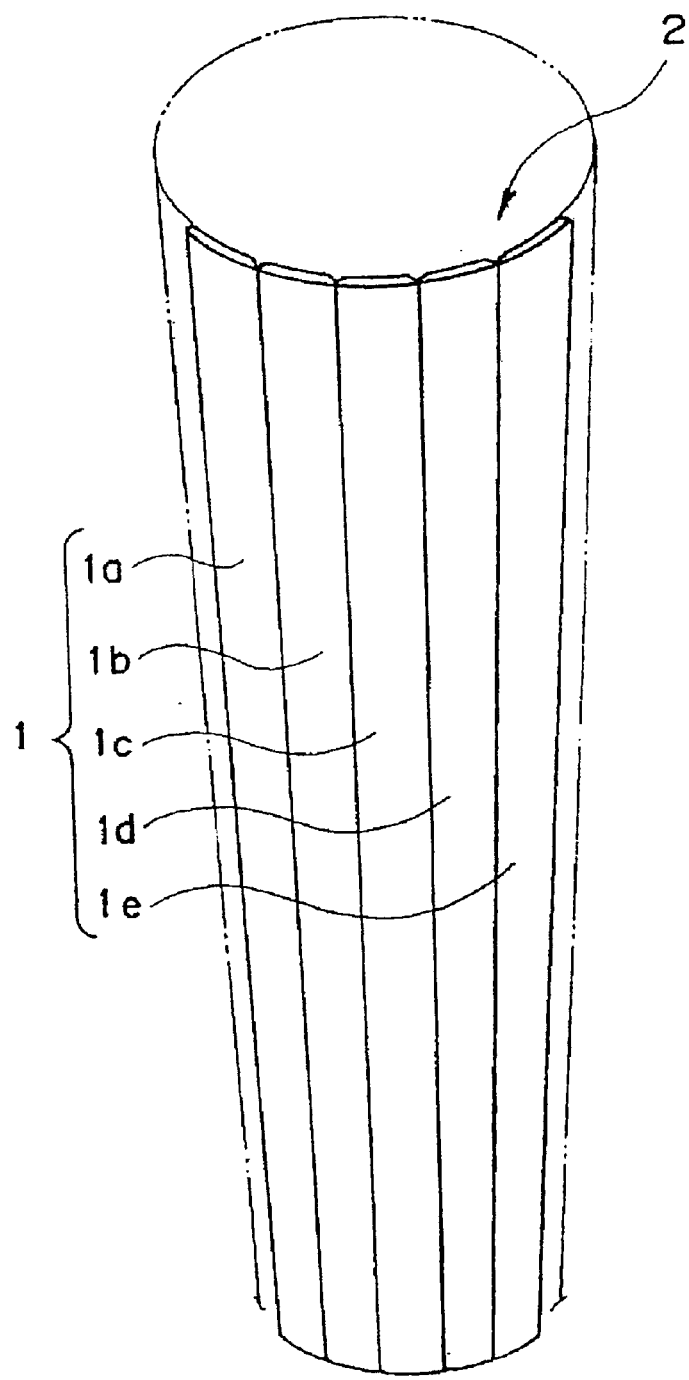
FIG. 2 is a perspective view illustrating schematically the state of operation of a decorative aid to be used for the method of cosmetic decoration as the second mode of embodiment of this invention.

Now, the second mode of embodying this invention will be described below with reference to FIG. 2. This mode of embodiment, i.e. a method for cosmetic decoration which produces the effect of making a leg look slender by strongly depositing a pigment on the opposite lateral sides of the leg and, at the same time, leaving the front side of the leg white will be described.

In this mode of embodiment, the suntan is produced by using a suntan aid 2 which is provided with a cover 1 formed in a cross section roughly resembling the letter U along the front side contour of a leg. This cover 1 is formed of a raw material impervious to the ultraviolet light and is composed of five cover pieces 1a–1e separated along the longitudinal direction thereof.

Now, the method for getting suntan by using this suntan aid 2 will be described below. The wish to get suntan by using this suntan aid is fulfilled by first fitting the cover 1 on the leg. The cover 1 is adapted to avoid covering the lateral sides of the leg. The leg in the consequently assumed state is exposed to the ultraviolet light on the front side and the lateral sides thereof. In this case, only the lateral sides of the leg are irradiated with the ultraviolet light. After the exposure to the ultraviolet light is continued for a fixed time, the two cover pieces 1a, 1e which are positioned on the opposite outer sides are removed. Then, the leg in the consequently assumed state is exposed to the ultraviolet light. In this case, not only the lateral sides of the leg but also the areas of the leg which have been hidden by the cover pieces 1a, 1e are exposed to the ultraviolet light. Then, after the exposure to the ultraviolet light has continued for a fixed time, the cover pieces 1b, 1d positioned at this time on the opposite outer sides are removed and the leg in the consequently assumed state is exposed to the ultraviolet light. In this case, the whole area excepting the part of the skin hidden by the cover piece 1c positioned on the front of the leg is fated to be exposed to the ultraviolet light. When the deposition of pigment is caused in this manner, the portions of the leg on the opposite lateral sides which have been exposed to the ultraviolet light for a long time are strongly sunburnt and the front portions of the leg remain white. According to this method, the portions of the skin binding the cover pieces 1a–1e are fated to produce boundary lines, though slightly, due to variations in the degree of suntan. These boundary lines pose no particular problem because they are faded in a matter of one to two days.

Third Mode of Embodiment

Figure 3:
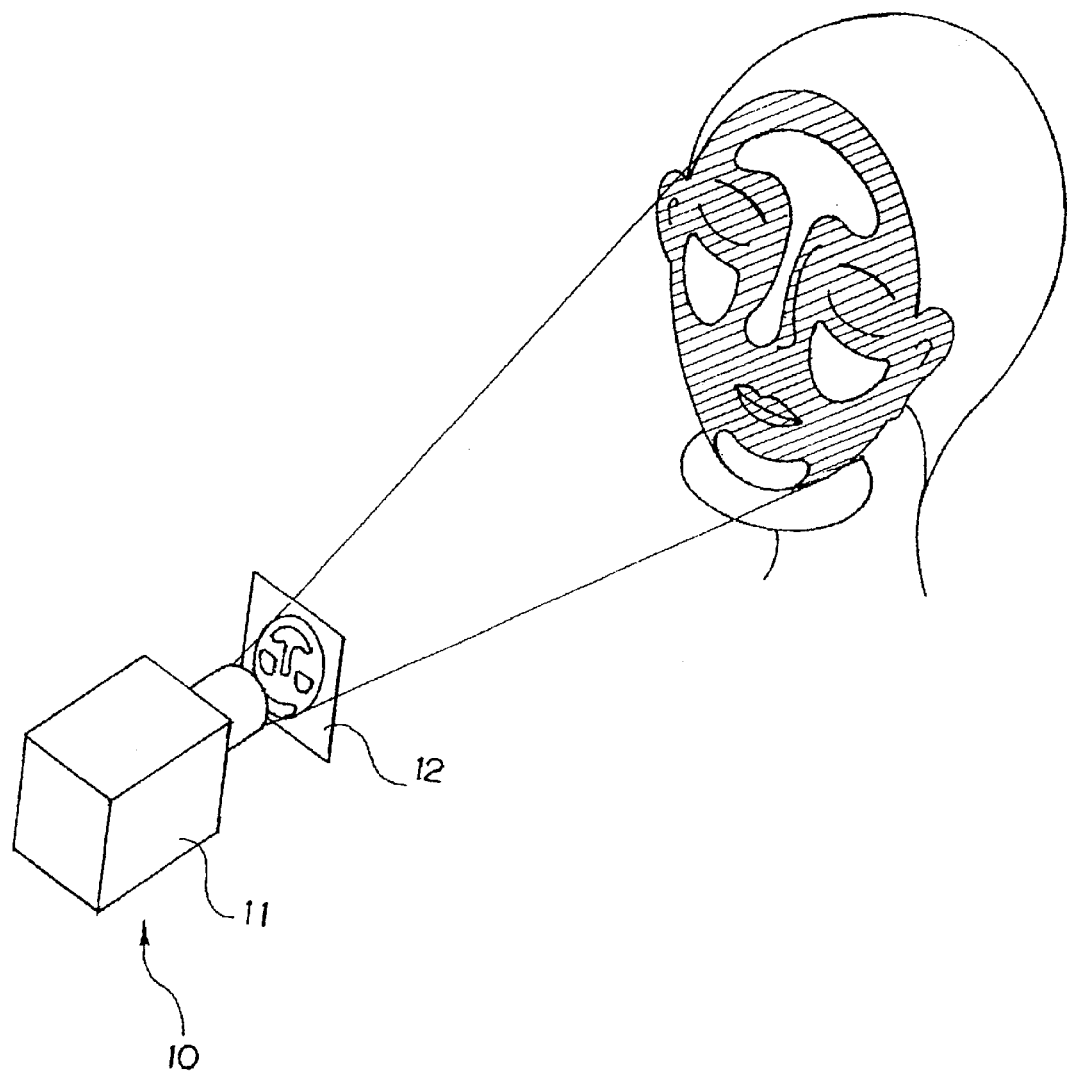
FIG. 3 is a perspective view illustrating schematically the state of operation of a projector to be used for the method of cosmetic decoration as the third mode of embodiment of this invention.

The projector as the third mode of embodiment of this invention will be described below with reference to FIG. 3. FIG. 3 illustrates a projector 10 which combines a projecting part 11 and a filter 12. This projector 10 has built therein a light source (not shown) serving the purpose of emitting a light containing the ultraviolet light. The filter 12 is adapted to pass the light emitted from the light source mentioned above and meanwhile control the light irradiating the face positioned at a prescribed distance from the projector 10 so as to increase the amount of the light reaching the lateral side parts of the face which are the areas expected to assume a darker color. Incidentally, this filter can be manufactured from an image portraying an ideal light and shade pattern. Alternatively, it can be manufactured by the white-to-black inversion of a picture obtained by actually photographing a person endowed with an ideal light and shade pattern.

Fourth Mode of Embodiment

Figure 4:
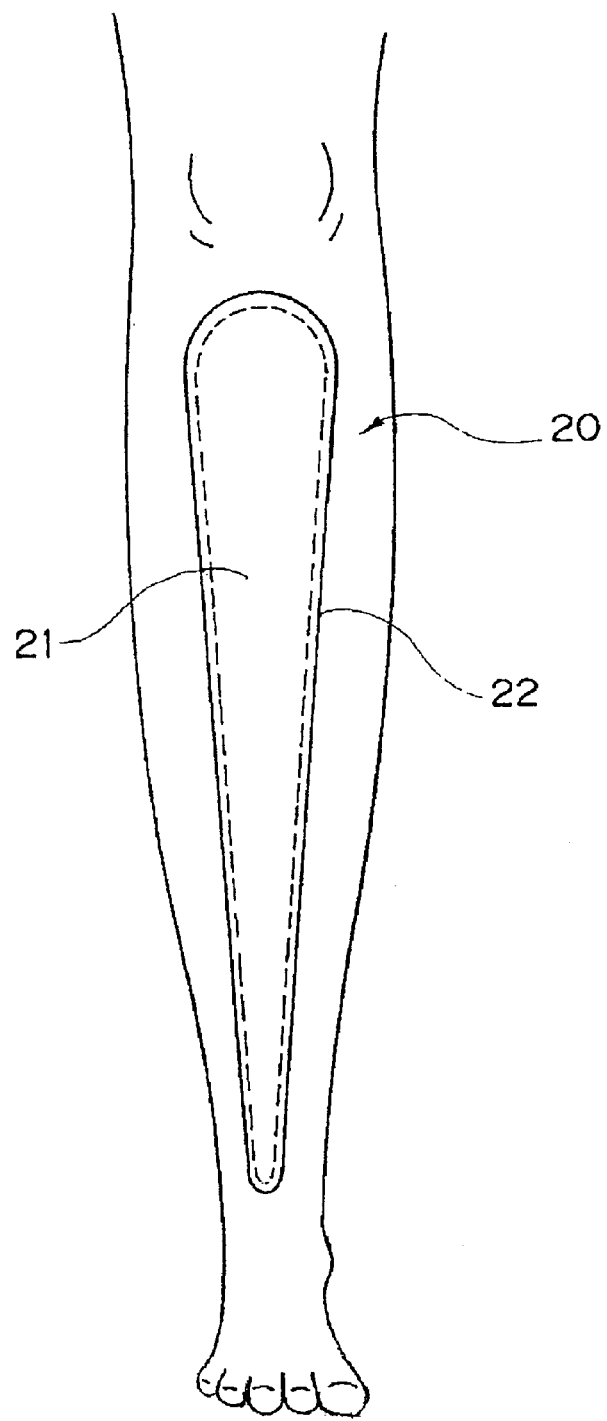
FIG. 4 is a perspective view illustrating schematically the state of operation of a pack to be used for the method of cosmetic decoration as the fourth mode of embodiment of this invention.

The fourth mode of embodiment of this invention will be described with reference to FIG. 4. Illustrated in FIG. 4 is a pack 20 of the shape of a tape adapted to impart light and shade to a leg. This pack 20 is formed of a sheet 21 to be used as applied to the front side of a leg. The sheet 21 is coated on the side thereof fated to adhere to the leg, though omitted from illustration, with hydroquinone as a whitening agent. Further, the peripheral part of the surface of the sheet 21 destined to adhere to the leg is provided along the curve thereof with an adhesive tape adapted to adhere to the leg. When this pack 20 is applied fast to the leg and then left standing for a while, the skin of the front of the leg assumes a bright color and the leg, owing to the difference of color from the opposite lateral sides thereof, is made to look slender. The method of using the whitening agent in the manner described above fits a person whose skin inherently has a dark color and, in this respect, differs from the first—third modes of embodiment which fit persons whose skins inherently have a dark color.

Fifth Mode of Embodiment

Figure 5:
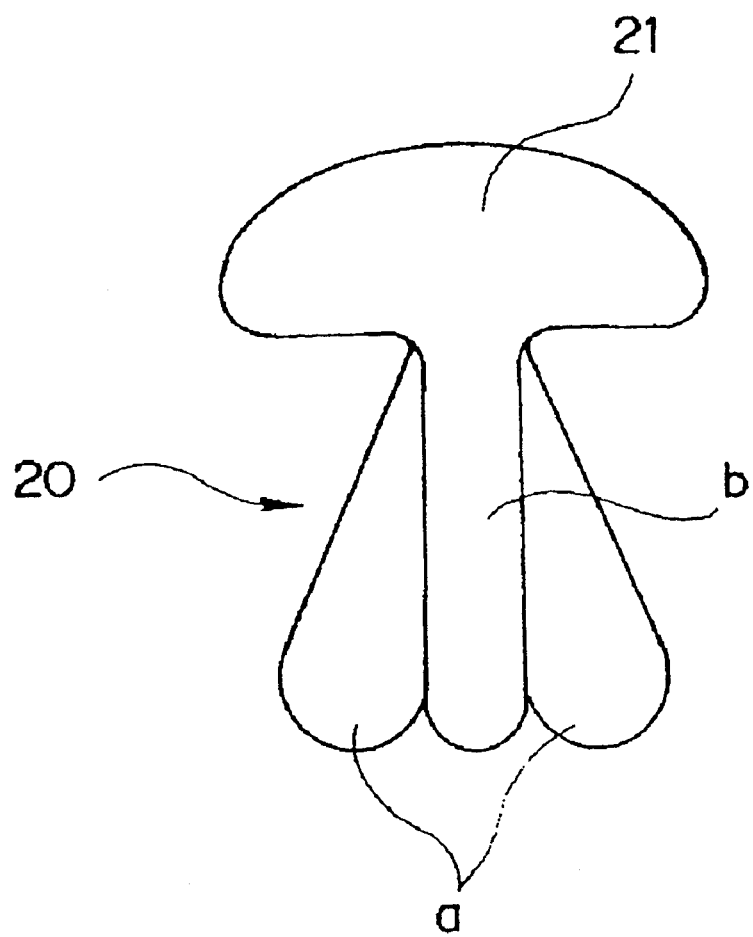
FIG. 5 is a perspective view illustrating schematically the state of operation of a pack to be used for the method of cosmetic decoration as the fifth mode of embodiment of this invention.

The fifth mode of embodiment of this invention will be described with reference to FIG. 5. FIG. 5 illustrates a pack 20 to be used for the purpose of making the T zone stand out in appearance. Since this pack 20 is used as applied fast to the T zone, it incorporates therein a sheet 21 which is formed in a shape substantially resembling the letter T. The side of this sheet 21 destined to adhere fast to the skin is impregnated with psoralen as a pigment deposition promoting agent and hydroquinone as a whitening agent. Specifically, the part of the sheet 21 indicated as a is impregnated with the pigment deposition promoting agent and the part thereof indicated as b is impregnated with the whitening agent. By repeating the act of fastening this pack to the T zone and allowing it to stand thereon for a while, therefore, the forehead and the bridge of the nose are made to stand out in a bright color and, at the same time, the opposite lateral sides of the nose are made to assume a dark color, with the result that the face will appear to have a shapely nose.

Sixth Mode of Embodiment

Figure 6:
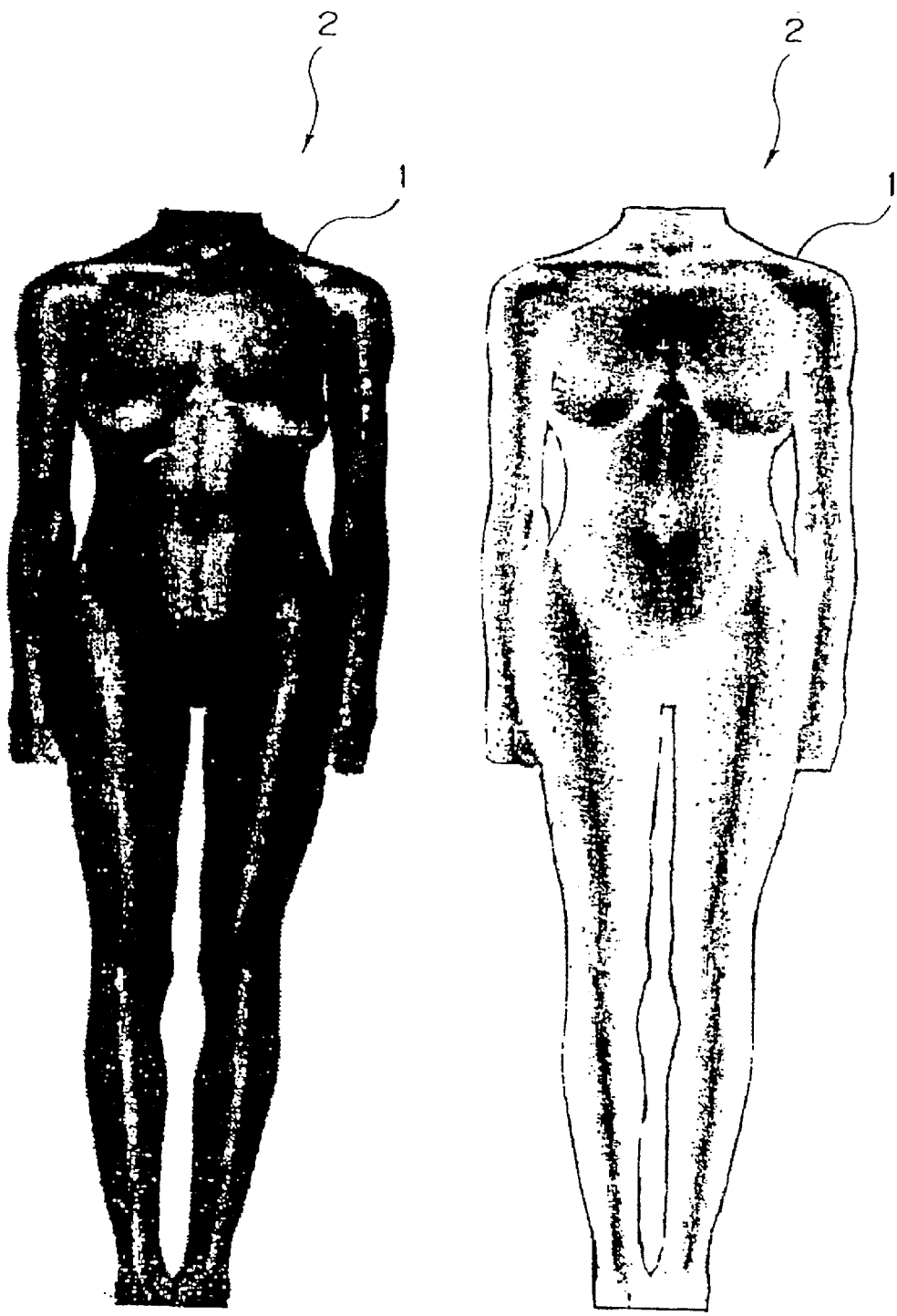
FIG. 6 is a front view illustrating a decorative aid to be used for the method of cosmetic decoration as the sixth mode of embodiment of this invention.

The sixth mode of embodiment of this invention will be described with reference to FIG. 6. This method concerns a technique for varying the degree of pigment deposition in different areas of the skin by using a laser beam. The method of this mode of embodiment, in irradiating the skin with the laser beam, uses a decorative aid 2 which is provided with a body suit 1 as a cover as illustrated in the diagram. The decorative aid 2 to be used in this method is prepared in two types as illustrated in the diagram. First, the decorative aid 2 illustrated on the left side in the diagram is formed of a transparent raw material adapted to resist passage of light more in the part of the skin requiring to assume a darker color. Then, the decorative aid 2 illustrated on the right side in the diagram is formed of a transparent raw material adapted to resist passage of light more in the part of the skin requiring to assume a brighter color. In the diagram, both the decorative aids 2 are illustrated so as to appear in a denser black color in the part resisting passage of light more.

The method for cosmetic decoration in this case is as follows. First, a person about to put up cosmetic decoration is made to wear the body suit illustrated on the left side in the diagram. The laser set under such conditions as to induce omission of pigment in the skin is made to irradiate the subject in the consequently assumed state so as to scan the whole body of the subject. This body suit is adapted to resist passage of light in the area of the skin requiring to assume a dark color as described above. The laser beam capable of inducing omission of pigment, therefore, is fated to reach only the area of the skin that requires to assume a bright color. Thus, the degree of pigment deposition decreases in the part of the skin requiring to be highlighted. Then, the person about to make cosmetic decoration is made to wear the body suit illustrated on the right side in the diagram. The laser set under such conditions as to induce deposition of pigment in the skin is made to irradiate the subject in the consequently assumed state so as to scan the whole body of the subject. This body suit 1 is adapted to resist passage of light in the area of the skin requiring to assume a bright color as described above. The laser beam capable of inducing omission of pigment, therefore, is fated to reach only the area of the skin that requires to assume a dark color. Thus, the degree of pigment deposition increases in the area of the skin requiring to assume a dark color. Incidentally, since the part of the body suit 1 illustrated on the right in the diagram which does not pass the laser beam partly overlaps the part of the body suit 1 illustrated on the left in the diagram which passes the light, the surface color in part of the area of the skin is fated to remain intact. According to the method described above, therefore, proper gradation is imparted to the boundary between the area made to assume a dark color and the area made to assume a light color by the exposure to the laser. By using the method of cosmetic decoration in the present mode of embodiment, it is made possible to attain in a very short span of time the same effect as is obtainable by performing a body make which normally last over several months.

Industrial Applicability

The method for cosmetic decoration contemplated by this invention utilizes the deposition of pigment as described above. The light and shade which is imparted by this method lasts for several days without being affected by perspiration or water, notwithstanding it brings the same effect as the foundation. Thus, this method can greatly alleviate the time and labor spent in the cosmetic decoration. Further, the light and shade obtained by the deposition of pigment assumes a perfectly natural tint because it is based on the color of the skin of the individual person. This method, therefore, is at an advantage in alleviating the burden of cosmetic decoration and allowing the effect of making the subject look slim to be more easily and naturally obtained than when the conventional foundation is used. Then, by using the decorative aid, projector, and pack according to this invention, it is made possible to attain the effect mentioned above more easily and accomplish the alleviation of the burden on the cosmetic decoration to a greater extent.

What is claimed is:

1. A method for achieving cosmetic decoration using light, comprising:
    providing a mask that covers a body part, the mask having portions corresponding to areas of the body part for which emphasis is more desired and areas of the body part for which emphasis is less desired, the mask having areas of lower transparency to ultraviolet light corresponding to the portions corresponding to the areas of the body part for which emphasis is more desired and areas of higher transparency to ultraviolet light corresponding to the portions corresponding to the areas of the body part for which emphasis is less desired;
    applying the mask to the body part; and
    exposing the body part to light such that the light passes through the mask to reach the body part,
    wherein a boundary between the areas of lower transparency and higher transparency is sufficiently gradated to prevent unnatural contrast between light and shade and to thereby emphasize a contour of the body part.

2. The method of claim 1, wherein the body part is a face.

3. The method of claim 2, wherein the areas of lower transparency together form a shape of a T zone.

4. A method of achieving the effect of the application of a foundation on a face, comprising:
    outlining a T zone against a surface of the face, the T zone being expected to assume a brighter color than any other area of the face;
    providing a mask capable of exposing the T zone to less ultraviolet light than any other area of the face; and
    exposing the face to light such that light and shade is imparted to surface color of the skin of the face sufficient to emphasize a contour of the face wherein the mask comprises material having different levels of transparency to ultraviolet light.

5. The method of claim 1, wherein a boundary between the different levels of transparency is gradated to prevent unnatural contrast between light and shade on the skin of the face.

* * * * *